ns Patent Number: 4,680,413
Date of Patent: Jul. 14, 1987

United States Patent
Genda et al.

[54] PROCESS FOR THE PRODUCTION OF 3-PHENYL-4-CYANOPYRROLES

[75] Inventors: Yoshikazu Genda, Syogawa; Hiroyuki Muro, Shinminato; Kiyoharu Nakayama, Himi; Yoshiaki Miyazaki; Yoshiji Sugita, both of Takaoka, all of Japan

[73] Assignee: Nippon Soda Co., Ltd., Tokyo, Japan

[21] Appl. No.: 814,893

[22] Filed: Dec. 30, 1985

[51] Int. Cl.$^4$ .................. C07D 207/34; C07D 405/04; C07D 207/22
[52] U.S. Cl. .................................... 548/526; 548/561; 548/565
[58] Field of Search .............................. 548/561, 526

[56] References Cited
PUBLICATIONS
YEBDRI, Tet. Letters 24, 369–372, (1983).

Primary Examiner—Mark L. Berch
Attorney, Agent, or Firm—George B. Oujevolk

[57] ABSTRACT

A process for the production of a compound having the formula:

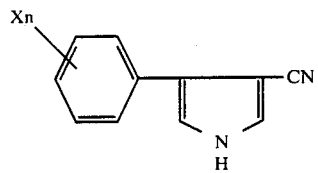

which comprises a reaction of a compound having the formula:

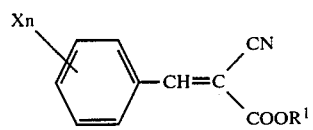

with a compound having the formula $R^2SO_2CH_2NC$ wherein
X is same or different substituent(s) selected from the group consisting of halogen, $C_{1-6}$ alkyl, $C_{1-6}$ haloalkyl, $C_{1-6}$ alkylamino, $C_{1-6}$ alkoxy, nitro, cyano and methylenedioxy;
$COOR^1$ is carboxylic acid or ester;
$R^2$ is $C_{1-10}$ cyclic hydrocarbon which may be substituted by substituent(s) not giving negative effects to said reaction;
n is 0, 1 or 2.

1 Claim, No Drawings

PROCESS FOR THE PRODUCTION OF 3-PHENYL-4-CYANOPYRROLES

The present invention relates to a novel process for the production of 3-phenyl-4-cyanopyrroles which are useful as an intermediates for medically active compound and agriculturally and horticulturally active compound.

The above-mentioned pyrrole derivatives are acylated, for example, at the 1-position to obtain compounds useful as agricultural and horticultural fungicides described in Jpn. Kokai Tokkyo Koho JP Nos. 81079672, JP 80051066, JP 80057508 and others.

The process for the production of 3-phenyl-4-cyanopyrrole is disclosed in Tetrahedron Letters No. 52, 5337-5340 (1972) as below.

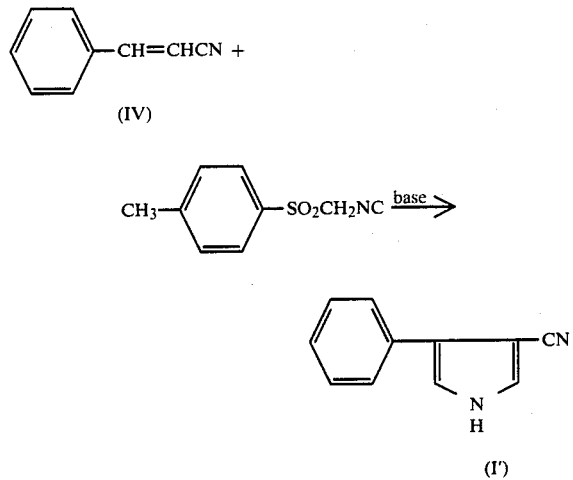

However, under this process, the yield is low, about 35%, because complicated purifying processes are needed to obtain compound (I'). Further, compound (IV) is undesirable as an industrial product in view of the fact that the compound is manufactured through decarboxylation of alpha-cyanocinnamic acids or the esters thereof the reaction conditions of which are rigorous and the purification process of the reaction mixture to obtain compound (IV) therefrom are complicated and need vacuum distillation or recrystallization, through which the yield of compound (IV) becomes very low. Therefore, this process is not a desirable commercial process.

The present invention relates to a process for the production of a compound having the formula:

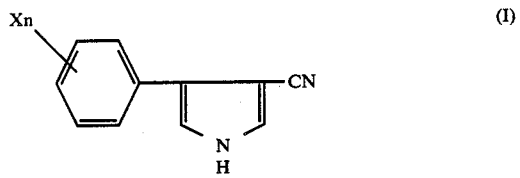

which comprises a reaction of a compound having the formula:

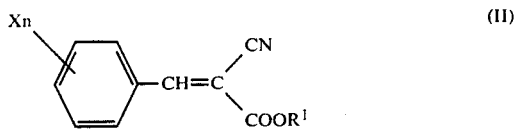

with a compound having the formula:

$$R^2SO_2CH_2NC \quad (III)$$

wherein

X is same or different substituent(s) selected from the group consisting of halogen, $C_{1-6}$ alkyl, $C_{1-6}$ haloalkyl, $C_{1-6}$ alkylamino, $C_{1-6}$ alkoxy, nitro, cyano and methylenedioxy;

$COOR^1$ is carboxylic acid or ester;

$R^2$ is $C_{3-10}$ cyclic hydrocarbon, which may be substituted by subtituent(s) not giving negative effects to said reaction;

n is 0, 1 or 2.

in an organic solvent in the presence of base(s).

As becomes clear from the reaction mechanism of the process of the present invention described later, each of $COOR^1$ radical in the compounds (II) and $R^2SO_2$ radical in the compounds (III) participates only at the intermediate stages of this reaction and is finally eliminated without any formation of residue(s) on the compounds (I). Therefore, $R^1$ and $R^2$ may be anything which does not negatively effect the reaction.

As $R_1$, hydrogen or a $C_{1-10}$ hydrocarbon which may be substituted by substituents which do not negatively effect the reaction; and $R_2$, a $C_{3-10}$ cyclic hydrocarbon which may be substituted by substituents which do not negatively effect the reaction.

The substituent(s) negatively effect the reaction are the substituent(s) reactive to $-N\equiv C$ of compounds (III) and/or Xn or compounds I and II, for example, isocyanato, isothiocyanato, amino, imino, mercapto and hydroxy radicals. The other substituent(s) which negatively effect the reaction are the substituents steric-hindering to the reaction. In other words, bulky and rigid substituents to block the contact of the reacting point(s). Accordingly, those radicals are excluded from the desirable substituents used at $R^1$ and $R^2$.

As the base(s), it is possible to use organic or inorganic bases such as sodium hydride, sodium alkoxide, potassium alkoxide, metallic sodium, sodium hydroxide, potassium hydroxide, potassium carbonate, sodium carbonate or the like.

As the organic solvent, it is possible to use benzene, toluene, ether, tetrahydrofuran, dimethylsulfoxide, dimethylformamide, dimethoxyethane or other aprotic solvent, when as the base(s), sodium hydride, sodium alkoxide, potassium alkoxide, or metallic sodium, is used, then dimethoxyethane is the best solvent in this case. In addition to the above specified organic solvents, it is also possible to use a lower alkyl alcohol, or a mixed solvent which is a mixture of a lower alkyl alcohol with halogen-containing solvent, if as the base(s), sodium hydroxide, potassium hydroxide, potassium carbonate, or sodium carbonate is used. In the lower alkyl alcohol, methanol, ethanol, isopropanol, n-propanol, isobutanol, n-butanol, t-butanol etc. are contained, and in the halogen-containing solvent, methylene dichloride, chloroform, carbontetrachloride, trichloroethane etc. are contained.

The reaction temperature varies with a combination of the raw materials, the kind of the bases, and the solvents, used, but normally it ranges between −30° C. and 100° C., a range of −10° C. to 40° C. may be more desirably used.

In the present invention, the reaction proceeds under mild conditions through the presumed reaction mechanisms as shown below, which are entirely different from those in the known manufacturing method.

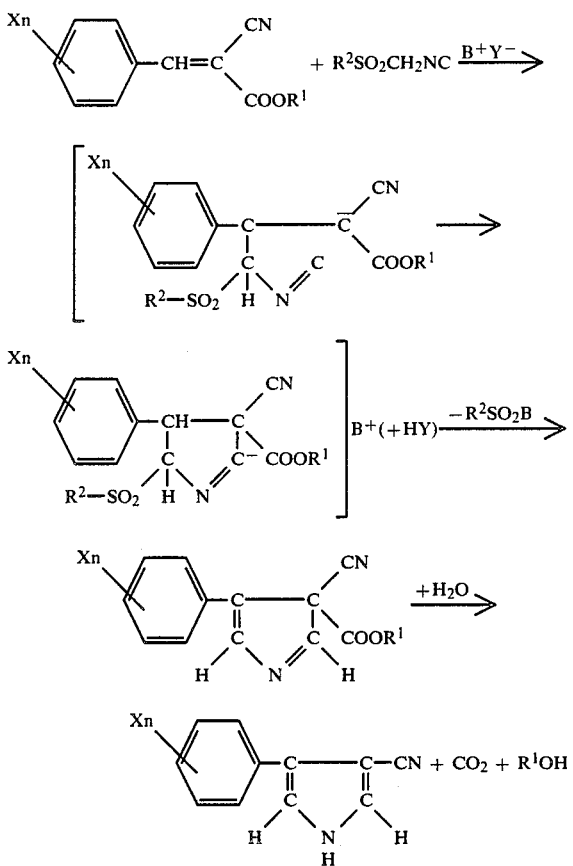

wherein B+ is base cation, Y− is counter anion to B+.

The following Examples illustrate the invention, but the invention should not be limited by those Examples.

EXAMPLE 1

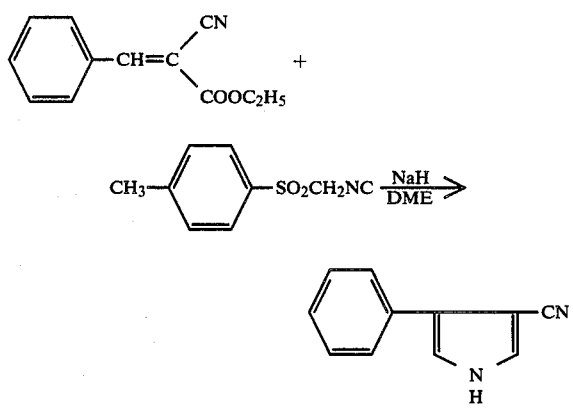

10.06 g (50.0 m mol) of alpha-cyanocinnamic acid ethyl ester and 10.25 g (52.5 m mol) of tosyl methylisocyanide were dissolved in a 80 ml solution of dried dimethoxyethane (hereunder often shortened to DME). The solution obtained was then fed dropwise, in a stream of N₂ gas at a temperature ranging from 0° C. to 5° C., into a 50 ml suspension of dried dimethoxyethane and 2.88 g (60.0 m mol) of 50% NaH to allow reactions to proceed.

After dropping, the mixed liquid was stirred for one hour at room temperature to complete the reaction. Then, to the reaction mixture 50 ml of water was added and then neutralized by 10% HCl to pH 8. From the neutralized mixture, dimethoxyethane was distilled off under reduced pressure, then 100 ml of water was further added thereto, and the mixture was stirred for 30 min. to precipitate crystals. The crystals were filtered off and washed with water and toluene and dried. As the result, 7.48 g of 3-phenyl-4-cyanopyrrole was obtained. Yield 88.9%, melting point 129°–130° C.

EXAMPLE 2

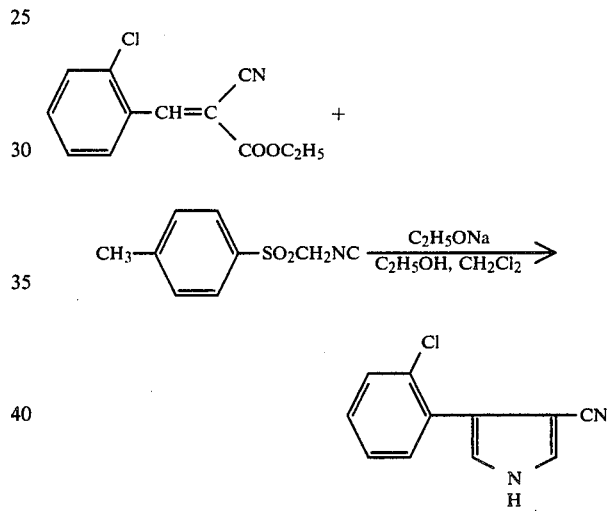

11.78 g (50.0 m mol) of alpha-cyano-O-chlorocinnamic acid ethyl ester was dissolved in 80 ml of ethanol. The solution obtained was then cooled at a temperature 0° C. to 3° C., before 4.08 g (60.0 m mol) of sodium ethoxide was added to it. After this, said solution was fed dropwise at a temperature from 0° C. to 3° C. with the solution obtained by dissolving 10.25 g (52.5 m mol) of tosyl methylisocyanide in 70 ml of methylene chloride and thus reaction was allowed to proceed, under stirring, for one hour in the same temperature range, before it completed. Then, to the reaction mixture 50 ml of water was added and neutralized to pH 8 by using 10% HCl. From the neutralized mixture, methylene chloride and ethanol were distilled out under reduced pressure, then 100 ml of water was further added thereto, and the mixture was stirred for 30 min. to precipitate crystals. The crystals were filtered out and washed with water and dried. As the result, 9.93 g of 3-(2-chlorophenyl)-4-cyanopyrrole was obtained. Yield 98.0%, melting point 138°–139° C.

EXAMPLE 3

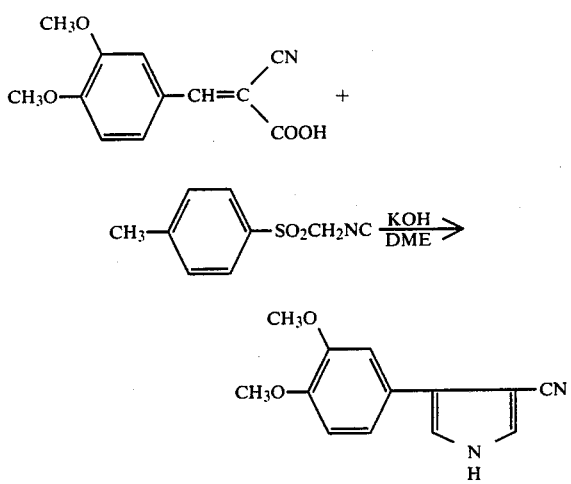

12.62 g (225.0 m mol) of potassium hydroxide was added to 100 ml of dimethoxyethane. The solution was then cooled at a temperature from 0° C. to 10° C., was fed with 11.66 g (50.0 m mol) of alpha-cyano-3,4-dimethoxycinnamic acid, and was stirred for 30 min. at the same temperature. The liquid was then fed dropwise for one hour, at room temperature, with a solution of 10.25 g (52.5 m mol) of tosyl methylisocyanide in 60 ml of dimethoxyethane. When the dropping ended, the mixed liquid was stirred for two hours at room temperature till the reaction completed. Then, to the reaction mixture 70 ml of water was added and neutralized to pH 8 by 10% HCl. From the neutralized mixture, dimethoxyethane was distilled off under reduced pressure, then 800 ml of water was further added thereto, and the mixture was stirred for 30 min. to precipitate crystals. The crystals were then filtered off and washed with water and dried. As the result, 10.50 g of 3-(3,4-dimethoxyphenyl)-4-cyanopyrrole was obtained. Yield 92.0%, Melting point 212°–214° C.

EXAMPLE 4

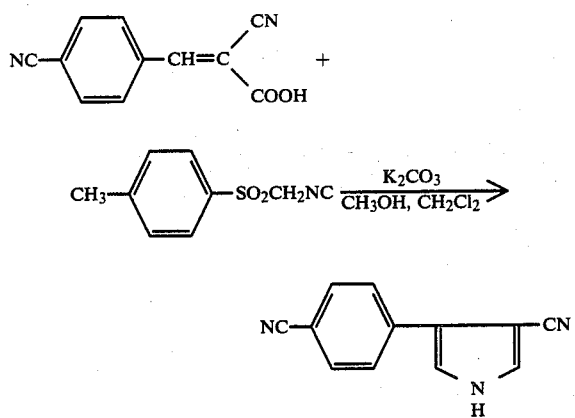

20.73 g (150.0 m mol) of potassium carbonate and 9.91 g (50.0 m mol) of alpha-cyano-p-cyanocinnamic acid were added to 80 ml of methanol and were stirred for 30 min at room temperature. The reaction liquid was then fed dropwise, at a temperature ranging between 30° C. and 40° C., with a solution of 10.25 g (52.5 m mol) of tosyl methylisocyanide in 70 ml of methylene chloride. After the dropping ended, the reaction mixture was further stirred for three hours at 40° C. to complete the reaction. Then, to the reaction mixture 50 ml of water was added and was neutralized to pH 8 by 10% HCl. From the neutralized mixture, methylene chloride and methanol were distilled off under reduced pressure, then, 100 ml of water was further added thereto, and the mixture stirred for 30 min. to precipitate crystals. The crystals were filtered off and washed with water and dried. As the result, 7.83 g of 3-(4-cyanophenyl)-4-cyanopyrrole was obtained. Yield 81.05%,
melting point 170°–172° C.

EXAMPLE 5

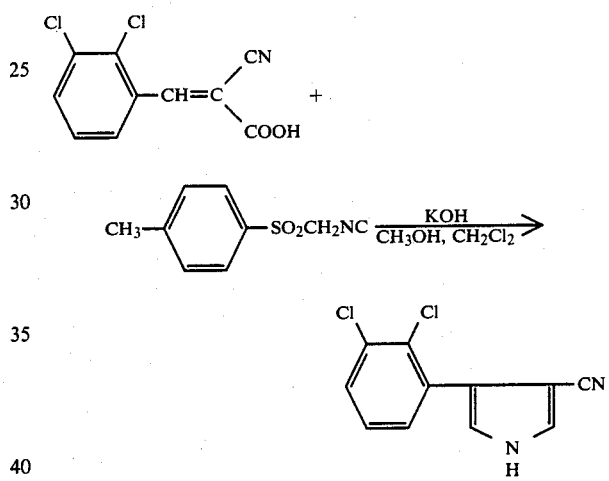

12.62 g (225.0 m mol) of potassium hydroxide was dissolved in 80 ml of methanol. While being cooled at a temperature 0° to 10° C., the solution was fed with 12.10 g (50.0 m mol) of alpha-cyano-2,3-dichlorocinnamic acid and the mixture was stirred for 20 min. in the same temperature range. A solution of 10.25 g (52.5 m mol) of tosyl methylisocyanide in 70 ml of methylene chloride was added dropwise, at a temperature from 0° to 5° C., to the above mixture. The reaction mixture was then stirred for 30 min. at the same temperature to complete the reaction. Then, to the reaction mixture 50 ml of water was added and was neutralized to pH 8 by 10% HCl. From the neutralized mixture, methylene chloride and methanol was distilled off under reduced pressure, then, 100 ml of water was further added thereto and the mixture was stirred for 30 min. to precipitate crystals. The crystals were filtered off and washed with water and dried. 11.73 g of 3-(2,3-dichlorophenyl)-4-cyanopyrrole was obtained. Yield 99.0%, Melting point 152°–153° C.

EXAMPLE 6-18

Reactions were allowed to go in the same procedures as Example 5. Table 1 shows the result.

TABLE 1

| example | material compound | product compound | yield (%) | melting point (°C.) |
|---|---|---|---|---|
| 6 | 2-(CF₃)C₆H₄-CH=C(CN)COOH | 4-(2-CF₃-C₆H₄)-3-cyanopyrrole | 97.3 | 106~107 |
| 7 | 2-F-C₆H₄-CH=C(CN)COOH | 4-(2-F-C₆H₄)-3-cyanopyrrole | 94.0 | 118~119 |
| 8 | 2-Br-C₆H₄-CH=C(CN)COOH | 4-(2-Br-C₆H₄)-3-cyanopyrrole | 95.0 | 143~145 |
| 9 | 3,4-(methylenedioxy)-C₆H₃-CH=C(CN)COOH | 4-(3,4-methylenedioxyphenyl)-3-cyanopyrrole | 92.1 | 191~193 |
| 10 | 2-NO₂-C₆H₄-CH=C(CN)COOH | 4-(2-NO₂-C₆H₄)-3-cyanopyrrole | 89.2 | 110~113 |
| 11 | 4-(N(CH₃)₂)-C₆H₄-CH=C(CN)COOH | 4-(4-N,N-dimethylaminophenyl)-3-cyanopyrrole | 92.3 | 148~150 |
| 12 | 2-CH₃-C₆H₄-CH=C(CN)COOH | 4-(2-CH₃-C₆H₄)-3-cyanopyrrole | 97.8 | 116~117 |
| 13 | 4-CH₃-C₆H₄-CH=C(CN)COOH | 4-(4-CH₃-C₆H₄)-3-cyanopyrrole | 85.7 | 139~141 |

TABLE 1-continued

| example | material compound | product compound | yield (%) | melting point (°C.) |
|---|---|---|---|---|
| 14 | 4-Cl-C6H4-CH=C(CN)(COOH) | 3-(4-Cl-C6H4)-4-CN-pyrrole (NH) | 90.1 | 149–150 |
| 15 | 3-Cl-C6H4-CH=C(CN)(COOH) | 3-(3-Cl-C6H4)-4-CN-pyrrole (NH) | 93.0 | 145–147 |
| 16 | 3-Br-C6H4-CH=C(CN)(COOH) | 3-(3-Br-C6H4)-4-CN-pyrrole (NH) | 89.6 | 130–133 |
| 17 | 3-NO2-C6H4-CH=C(CN)(COOH) | 3-(3-NO2-C6H4)-4-CN-pyrrole (NH) | 87.6 | 218–222 |
| 18 | 2-OCH3-C6H4-CH=C(CN)(COOH) | 3-(2-OCH3-C6H4)-4-CN-pyrrole (NH) | 99.0 | 134–136 |

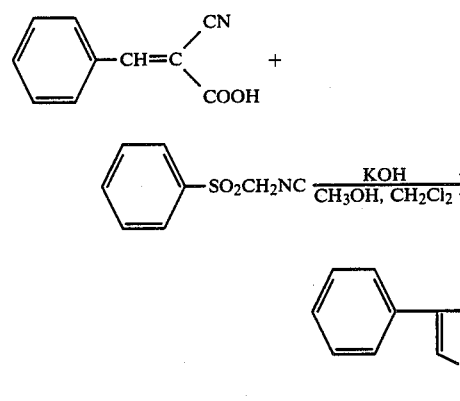

26.30 g (450 m mol as purity of 96%) of potassium hydroxide was dissolved in 200 ml of methanol. While being cooled at a temperature from 0° to 5° C., 17.30 g (100 m mol) of alpha-cyanocinnamic acid are added for 60 min. into the solution under stirring in the same temperature range. To the reaction mixture thus obtained under stirring at a temperature from 0° C. to 2° C., a solution of 18.48 g (102 m mol) of phenylsulfonyl methylisocyanide in 180 ml of methylene chloride was added dropwise for 70 min. The reaction mixture was then stirred for 3 hours at the same temperature. Then, to the reaction mixture 200 ml of water was added and neutralized to pH 8 by 10% HCl. From the neutralized mixture, methylene chloride and methanol was distilled off under reduced pressure, then 200 ml of water was further thereto, and the mixture was stirred for 40 min. to precipitate crystals. The crystals were filtered off and washed with water and dried. 12.65 g of 3-phenyl-4-cyanopyrrole was obtained. Yield 75.2%, melting point 129°–130° C.

EXAMPLE 20

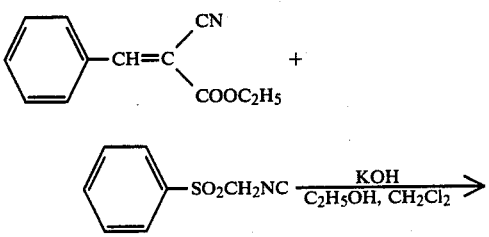

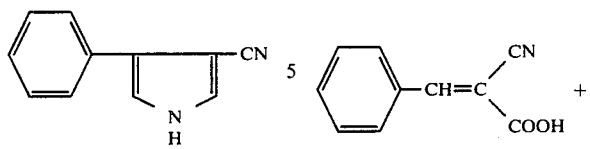

26.30 g (450 m mol as purity of 96%) of potassium hydroxide was dissolved in 200 ml of ethanol. While being cooled at a temperature from 5° C. to −3° C., 20.10 g (100 m mol) of alpha-cyanocinnamic acid ethyl ester are added for 5 min. into the solution under stirring in the same temperature range. To the reaction mixture thus obtained under stirring in the same temperature range, a solution of 18.48 g (102 m mol) of phenylsulfonyl methylisocyanide in 180 ml of methylene chloride was added dropwise for 60 min. The reaction mixture was then stirred for 2 hours at the same temperature to complete the reaction.

Thereafter, post-treatments were conducted by similar method as described in Example 19. 13.20 g of 3-phenyl-4-cyanopyrrole was obtained.

Yield 78.5%, Melting point 129°-130° C.

EXAMPLE 21

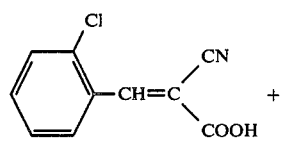

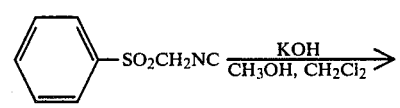

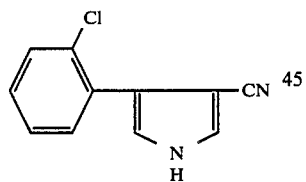

26.30 g (450 m mol as purity of 96%) of potassium hydroxide was dissolved in 200 ml of methanol. While being cooled at a temperature from 0° C. to 5° C., 20.76 g (100 m mol) of alpha-cyano-O-chlorocinnamic acid are added for 60 min. into the solution under stirring in the same temperature range. To the reaction mixture thus obtained under stirring in the same temperature range, a solution of 18.48 g (102 m mol) of phenylsulfonyl methylisocyanide in 200 ml of methylene chloride was added dropwise for 70 min. The reaction mixture was then stirred for 30 min. at the same temperature to complete the reaction.

Thereafter, post-treatments were conducted by similar method as described in Example 19. 19.85 g of 3-(2-chlorophenyl)-4-cyanopyrrole was obtained. Yield 98.0%, Melting point 138°-139° C.

EXAMPLE 22

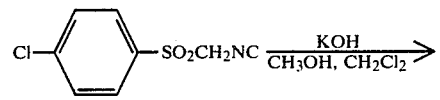

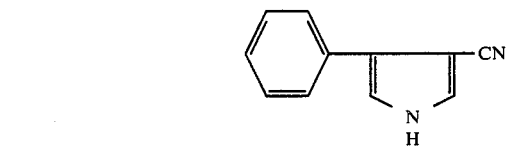

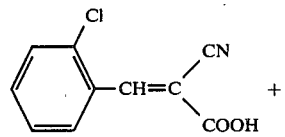

26.30 g (450 m mol as purity of 96%) of potassium hydroxide was dissolved in 200 ml of methanol. While being cooled at a temperature from 0° C. to 5° C., 17.30 g (100 m mol) of alpha-cyano-cinnamic acid are added for 30 min. into the solution under stirring in the same temperature range. To the reaction mixture thus obtained under stirring in the same temperature, a solution of 22.00 g (102 m mol) of 4-chlorophenylsulfonyl methylisocyanide in 220 ml of methylene chloride was added dropwise for 70 min. The reaction mixture was then stirred for 2 hours in the same temperature range to complete the reaction.

Thereafter, post-treatments were conducted by similar method as described in Example 19. 15.00 g of 3-phenyl-4-cyanopyrrole was obtained.

Yield 89.2%, Melting point 129°-130° C.

EXAMPLE 23

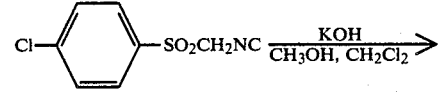

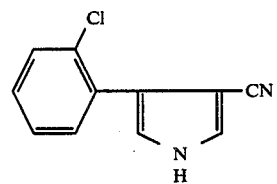

26.30 g (450 m mol as purity of 96%) of potassium hydroxide was dissolved in 200 ml of methanol. While being cooled at a temperature from 0° C. to 5° C., 20.76 (100 m mol) of alpha-cyano-O-chlorocinnamic acid are added for 40 min. into the solution under stirring in the same temperature range. To the reaction mixture thus obtained under stirring in the same temperature range, a solution of 22.00 g (102 m mol) of 4-chlorophenylsulfonyl methylisocyanide in 220 ml of methylane chloride was added dropwise for 40 min. The reaction mixture was then stirred for 2 hours at the same temperature to complete the reaction.

Thereafter, post-treatments were conducted by similar method as described in Example 19. 19.85 g of 3-(2-chlorophenyl)-4-cyanopyrrole was obtained. Yield 98.0%, Melting point 138°–139° C.

EXAMPLE 24

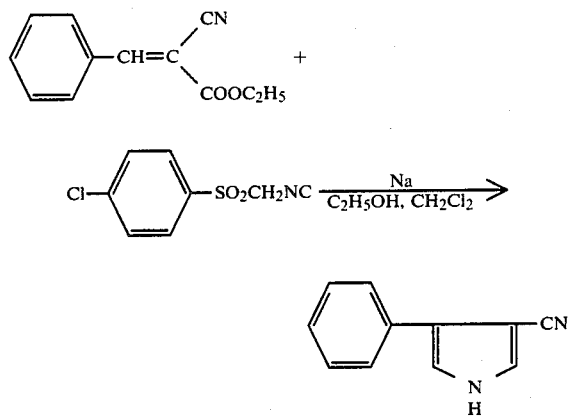

Sodium ethylate solution was prepared from 200 ml of ethanol and 4.60 g (200 m mol) of metallic sodium. While being cooled at a temperature from −3° C. to −2° C., 20.10 g (100 m mol) of alpha-cyano-cinnamic acid ethyl ester are added into the solution under stirring. To the reaction mixture thus obtained under stirring in the same temperature range, a solution of 22.20 g (103 m mol) of 4-chlorophenylsulfonyl methylisocyanide in 210 ml of methylene chloride was added dropwise for 40 min. The reaction mixture was then stirred for 3 hours at the same temperature to complete the reaction.

Thereafter, post-treatments were conducted by similar method as described in Example 19. 16.00 g of 3-phenyl-4-cyanopyrrole was obtained Yield 95.1%, Melting point 129°–130° C.

What we claim is:

1. A process for the production of a compound having the formula:

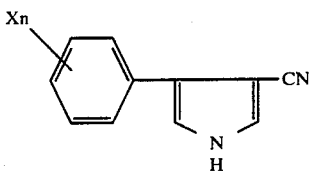

which comprises a reaction of a compound having the formula:

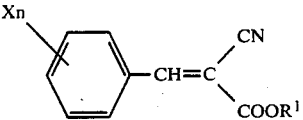

with a compound having the formula

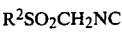

wherein

X is same or different substituent(s) selected from the group consisting of halogen, $C_{1-6}$alkyl, $C_{1-6}$haloalkyl, $C_{1-6}$alkylamino, $C_{1-6}$alkoxy, nitro, cyano and methylenedioxy;

$COOR^1$ is carboxylic acid or ester;

$R^2$ is $C_{3-10}$cyclic hydrocarbon which may be substituted by substituent(s) not giving negative effects to said reaction;

n is 0, 1 or 2.

in an organic solvent in the presence of base(s).

* * * * *